United States Patent [19]
Meiklejohn et al.

[11] Patent Number: 5,447,838
[45] Date of Patent: Sep. 5, 1995

[54] PROTEIN-DYE CONJUGATE FOR CONFIRMATION OF CORRECT DILUTION OF CALIBRATORS

[75] Inventors: Bruce Meiklejohn, San Diego; Michael Chiapetta, San Marcos, both of Calif.

[73] Assignee: Hybritech Incorporated, San Diego, Calif.

[21] Appl. No.: 925,513

[22] Filed: Aug. 5, 1992

[51] Int. Cl.⁶ ................ G01N 33/569; G01N 33/573; G01N 33/574
[52] U.S. Cl. ......................................... 435/5; 435/6; 435/7.1; 435/7.2; 435/7.21; 435/7.23; 435/7.4; 435/7.92; 435/7.93; 435/7.94; 435/7.95; 435/967; 436/8; 436/10; 436/56; 436/501
[58] Field of Search ...................... 435/967, 5, 6, 7.1, 435/7.2, 7.21, 7.92, 7.93, 7.94, 7.95, 7.23, 7.4; 436/501, 506, 570, 8, 10, 56

[56] References Cited

U.S. PATENT DOCUMENTS

| | | |
|---|---|---|
| 4,366,241 | 12/1982 | Tom et al. |
| 4,376,110 | 3/1983 | David et al. |
| 4,446,122 | 5/1984 | Chu et al. |
| 4,486,530 | 12/1984 | David et al. |
| 4,703,017 | 10/1987 | Campbell et al. |
| 5,068,181 | 11/1991 | Driscoll ............................ 435/13 |
| 5,120,662 | 6/1992 | Chen et al. |
| 5,166,074 | 11/1992 | Vessey et al. ................... 436/103 |
| 5,260,025 | 11/1993 | Covington et al. ............... 422/56 |
| 5,306,622 | 4/1994 | Mangold ........................ 435/7.92 |
| 5,334,502 | 8/1994 | Sangha ........................... 435/7.21 |
| 5,387,503 | 2/1995 | Selmer ................................ 435/5 |

FOREIGN PATENT DOCUMENTS 327163 8/1989 European Pat. Off.

OTHER PUBLICATIONS

Molecular Probes' "Handbook of Fluorescent Probes and Research Chemicals", (Catalogue) 1989, pp. 23-26 and pp. 92-94.
Wong, Shan, S., "Chemistry of Protein Conjugation and Cross-Linking," CRC Press 1991 pp. 27-48.
Zollinger, "Color Chemistry: Syntheses, Properties and Applications of Organic Dyes and Pigments," VCH Publishers, N.Y. 1987, pp. 305-319 Chapter 15.
Tietz, N., "Fundamentals of Clinical Chemistry", Ed. W. B. Saunders Co., Philadelphia, 1970 at pp. 930-924.
Gelderblom et al., Virology, 156: 171-176 (1987).
Wang et al., "Purification of Human Prostate Specific Antigen, "Invest. Urol. 17:159 (1979).
A directional insert having the revision date Feb. 1992, entitled "TANDEM®-R PSA ImmunoRadioMetric Assay for The Quantitative Measurement of Prostate-Specific Antigen (PSA) in Serum" pp. 1 through 7 by Hybritech Incorporated.
A directional insert having the revision date Mar. 1991, entitled "TANDEM®-E PSA ImmunoEnzyMetric Assay for the quantitative Measurement of Prostate-Specific Antigen (PSA) in Serum" pp. 1 through 8 by Hybritech Incorporated.
A directional insert having the revision date Jan. 1989, entitled "TANDEM®-R CEA ImmunoRadioMetric Assay for the Quantitative Measurement of Carcinoembryonic Antigen (CEA) in Serum" pp. 1 through 8 by Hybritech Incorporated.
A directional insert having the revision date Mar. 1989,
(List continued on next page.)

*Primary Examiner*—David Saunders
*Attorney, Agent, or Firm*—Donald J. Pochopien; Paul C. Steinhardt

[57] ABSTRACT

The present invention has multiple aspects that include an intermediate composition (i.e., a marked stock calibrator solution) for preparing diluted calibrator solutions that are marked in proportion to the amount of calibrator contained therein; a diluted (i.e., working) calibrator solution made therefrom, a series of diluted calibrator solutions that are visually colored in proportion to the concentration of calibrator therein; a method for performing a diagnostic assay that employs a series of marked calibrator solutions; a method for confirming that a stock solution of calibrator has been diluted correctly; and a method for indirectly confirming the concentration of calibrator in a working calibrator solution.

60 Claims, No Drawings

OTHER PUBLICATIONS
entitled "TANDEM®-E CEA ImmunoEnzyMetric Assay for the Quantitative Measurement of Carcinoembryonic Antigen (CEA) In Serum" pp. 1 through 8 by Hybritech Incorporated.
Schleif et al (1981) Practical Methods in Molecular Biology, Springer-Verlag, N.Y. pp 195–197.

Fisher Cataloge (1988) Fisher Scientific, Pa. p. 802.
Lim et al (1990) J. Immunol. Meth 135:9–14.
Sigma Catalogue (1992) Syma Chemicals, St. Louis, Mo., pp. 1650–1652.
Product Notification, Chem Track, Medical Analysis System (Apr. 1990), Camarillo, Calif.

PROTEIN-DYE CONJUGATE FOR CONFIRMATION OF CORRECT DILUTION OF CALIBRATORS

BACKGROUND OF THE INVENTION

A. Field Of The Invention

The present invention is directed to a method for determining the correct dilution of a calibrator solution, any calibrator solution, such as provided in a test kit, particularly a diagnostic test kit. More particularly, the present invention is directed to a method for conveniently determining the quantity or concentration of a calibrator in a solution that has been diluted from a stock solution of calibrator. The present invention is useful because it provides a convenient method by which a manufacturer of a calibrator solution can confirm the correct dilution of any calibrator solution that is made from an original stock solution. The present invention is especially useful where the calibrator material is an antigen or an antibody.

B. Background

Test kits for the analysis of a chemical or biochemical analyte are often provided with one or more solutions containing different concentrations of the analyte that are used to generate a calibration curve, i.e., "calibrator solutions." In these calibrator solutions, the analyte, or occasionally a chemically similar material (i.e., an analog), is used as the calibration material. During the commercial manufacturing of a solution containing a calibrator, the manufacturer often prepares a concentrated solution containing a predetermined amount of calibrator ("the stock solution"). The concentration of the calibrator material in this stock solution is precisely analyzed. Thereafter, and as needed, the manufacturer would prepare a diluted solution of the calibrator (i.e., a "working solution"), such as provided in a test kit, by diluting a precise aliquot of the stock solution to a precise volume. In many test kits, the manufacturer is required to prepare a series of calibrator solutions that encompass the working range of the test kit for the analyte of interest.

It is insufficient for any manufacturer of calibrator solutions to assume that all dilutions were made correctly from an original stock solution. The calibrator solutions must be subject to a quality control process to confirm that the dilutions of the stock solution to produce a working series of calibrator solutions were performed correctly. This is particularly true where the calibrator solution(s) is (are) part of a diagnostic test kit that provides the user with information upon which medical or veterinary decisions are made.

In many diagnostic test kits, the analyte is a complex antigenic molecule. To assure correspondence between the analyte and the calibrator material, the analyte is preferably the same as the calibrator material in the calibrator solutions. Conventional quality control ("Q.C.") and quality assurance ("Q.A.") analysis by a kit manufacturer for such analytes in a calibrator solution is complex, requires expensive reagents, and occasionally requires a long time (i.e., up to three days). Many diagnostic test kits, particularly those that provide a quantitative result, have up to six solutions that span a range of calibrator concentrations. In these multi-calibrator kits, the conventional analysis of the calibrator solutions by the kit's manufacturer is very costly and labor intensive. It is also an object of the present invention to provide a quick, simple, and reliable method that allows a kit manufacturer to confirm that a stock solution of a complex calibrator material, such as a ligand or antiligand, was diluted correctly during the manufacturing of working solutions of the calibrator. It is a further object of the present invention to provide a method for Q.C. or Q.A. by a kit manufacturer that neither requires a complex antigen antibody reaction nor multiple reaction sequences.

Currently, there are a variety of commercially available test kits. Each kit measures its respective analyte of interest using any one of a variety of signal-producing systems. These signal-producing systems include colorimetric, fluorimetric, phosphorescent, radiolabeling, chemiluminescent and the like. Accordingly, it is a further object of the present invention to provide a method for confirmation of the dilution of the stock calibrator solution that is accurate yet does not interfere with the signal used to measure the presence or concentration of the analyte.

Most manufacturers of calibrator solutions also manufacture "control solutions." Like calibrator solutions, control solutions are also prepared by precise dilution of a known amount of a stock solution that contains the control material. Whether a solution is a calibrator solution or a control solution is generally a matter of designation by the manufacturer. Accordingly, it is a further object of the present invention to provide a method that allows a kit or component manufacturer to confirm that a stock solution containing a control material was diluted accurately.

The ultimate user of a diagnostic test kit that contains calibration and/or control solutions is a diagnostic laboratory. The medical technologist in such a laboratory is often faced with the task of performing a number of diagnostic test procedures concurrently. One of the critical parts of any diagnostic test procedure is the maintenance of correct specimen identification. Prior to the pipetting step, the calibrator solutions, control solutions and patient samples are lined up in a precise sequence that gets logged in. Because one calibration solution looks like another, there is the possibility that the technologist, under the stress of performing multiple tasks, may transpose the alignment of one or more calibrator and/or control solutions. Further, a solution may inadvertently be mispipetted altogether. Once the calibrator and/or control solutions have been pipetted into an individual test tube, the chance of detecting and timely correcting the error before running the assay becomes even more remote. Many diagnostic assays have multiple steps and require from hours to days to complete before an error in transposition or pipetting would be detected.

Accordingly, it is an object of the present invention to also provide a method whereby a technologist or user of a diagnostic test kit would, in a timely fashion, detect and correct a pipetting error or transposition prior to a complete running of the diagnostic assay.

SUMMARY OF THE INVENTION

The present invention is directed to an indirect method for confirming the accuracy of one or more dilutions of a stock solution that contains a calibration or control material ("calibrator") for use in an assay for an analyte of interest. The method of the present invention is convenient and accurate because it uses, as an intermediate, a stock solution of a calibrator that further contains a defined quantity of a marker that is more conveniently and/or accurately measured than the calibrator itself. According to the present invention, once the initial concentration of a calibrator in a stock solution is known, all subsequent concentrations of the calibrator in solutions that are diluted therefrom (i.e., working solutions) are determined by measuring the marker and not the calibrator.

Thus, the present invention has multiple aspects. In its first aspect, it is directed to an intermediate composition for facilitating a determination that a stock solution containing a calibrator dissolved therein has been diluted correctly. The intermediate solution comprises a stock solution having dissolved therein:

a) a calibrator designated for use in calibrating or controlling an assay for an analyte of interest over a concentration range that the assay is designed to measure; and b) an identifiably effective and non-interfering amount of a marker dissolved therein for identifying a dilution level of the stock solution over the working concentration range of the calibrator, the marker neither participating as a reactant nor as a label on a reactant in the assay for the analyte of interest.

In its second aspect, the present invention is directed to a method for confirming the correct dilution of a stock solution containing a calibration or control material ("calibrator") comprising the steps of:

a. combining an identifiably effective and non-interfering amount of a marker and a predetermined quantity of a calibrator to form a marked stock calibrator solution having a first concentration of the marker and a second concentration of the calibrator;

b. calculating a proportion between the first concentration of the marker and the second concentration of the calibrator in the marked stock calibrator solution;

c. diluting the marked Stock calibrator solution or a portion thereof by a predetermined amount to produce a diluted calibrator solution wherein the proportion is substantially maintained, the diluted calibrator solution having a first expected concentration of the marker that is associated with a first expected physical parameter and further having a second expected concentration of the calibrator;

d. measuring an actual physical parameter of the diluted calibrator solution, the actual parameter being proportional to the actual concentration of the marker therein; and e. comparing the actual physical parameter or derivative thereof against the first expected physical parameter or derivative thereof respectively to confirm that the diluting step was performed correctly. The preferred derivatives of the actual physical parameter and the expected physical parameter are the actual concentration and the expected concentration, respectively, that are calculated therefrom.

Because the concentration of the marker in the stock calibrator solution is capable of being mathematically related to the concentration of calibrator therein, a determination of the actual concentration of marker in the diluted calibrator solution allows for a determination of the actual concentration of the calibrator in the diluted calibrator solution. Moreover, it also allows for confirmation that any difference between the expected concentration and the actual concentration of calibrator in the diluted calibrator solution is within acceptable limits. Accordingly, in its third aspect, the present invention is also directed to a method for indirectly confirming the concentration of a calibrator in a working solution, the method comprising:

a. combining an identifiably effective and a non-interfering amount of a marker and a predetermined quantity of a calibrator to form a marked stock calibrator solution having a first concentration of said marker and a second concentration of said calibrator;

b. calculating a proportion between the first concentration of the marker and the second concentration of the calibrator in the marked stock calibrator solution;

c. diluting the marked stock calibrator solution or a portion thereof by a predetermined amount to produce a diluted calibrator solution wherein the proportion is substantially maintained, the diluted calibrator solution having a first expected concentration of the marker that is associated with a first expected physical parameter and further having a second expected concentration of the calibrator;

d. measuring an actual physical parameter of the diluted calibrator solution, the actual physical parameter being proportional to the actual concentration of the marker in the diluted calibrator solution; and e. confirming that the actual concentration of calibrator in the diluted calibrator solution is substantially near its expected concentration by reference to a difference between the actual physical parameter and the first expected physical parameter or by reference, to a difference between derivatives thereof.

Although the phrase "calibrator solution" is used above, the phrase is meant to also include a "control solution" i.e., a solution that is used to verify the accuracy (e.g., viability) of an assay for an analyte of interest.

The present invention is also directed to a diluted (i.e. working) calibrator solution that is prepared from the intermediate composition position (i.e., stock solution) of the present invention when the marker therein is a visible dye.

The diluted calibrator solution is characterized by being one member of a series of diluted calibrator solutions, each diluted calibrator solution having therein both a predetermined concentration of a calibrator and a visible quantity of a colored marker, the visible quantity of the marker also being proportional to the concentration of calibrator therein; the series of calibrator solutions comprising a plurality of individual calibrator solutions that, as a series, span a range of calibrator concentrations and a corresponding range of marker concentrations, each solution in said series having a color intensity in proportion to the concentration of calibrator therein.

DETAILED DESCRIPTION OF THE INVENTION

The present invention has multiple aspects that include an intermediate composition (i.e., a marked stock calibrator solution) for preparing diluted calibrator solutions that are marked in proportion to the amount of calibrator contained therein; a diluted (i.e., working) calibrator solution made therefrom, a series of diluted calibrator solutions that are visually colored in proportion to the concentration of calibrator therein; a method for performing a diagnostic assay that employs a series of marked calibrator solutions; a method for confirming that a stock solution of calibrator has been diluted correctly; and a method for indirectly confirming the concentration of calibrator in a working calibrator solution.

In its first aspect, the present invention is directed to an intermediate composition for facilitating a determination that a stock solution, any stock solution, containing a calibration or control material ("calibrator") dissolved therein has been diluted correctly. Preferably, the present invention is directed to a composition for facilitating a determination that a stock solution containing a calibrator for a diagnostic assay in the human veterinary, and agricultural fields, particularly immunoassay, has been diluted correctly. The intermediate composition comprises a stock solution having dissolved therein:

a) a calibrator designated for use in calibrating or controlling an assay for an analyte of interest over a working concentration range i.e., a concentration range to be measured by the assay; and b) an identifiably effective amount of a marker dissolved therein for identifying a dilution level of the stock solution over the working concentration range of the calibrator, said marker neither participating as a reactant nor as a label on a reactant in said assay for said analyte.

By the word "controlling," as used in element (a) above, is meant utilizing providing one or more control materials (i.e., materials with a known concentration of analyte) for validating the results of the assay.

For purposes of this invention, a "stock solution" is meant to include any solution containing a known amount of a solute of interest (i.e., a calibrator) that is intended to be used as a source for producing more dilute solutions (i.e., working calibrator solutions) containing the solute of interest. The stock solution may be an organic or an aqueous based solution or a mixture of both. Preferably, the stock solution is an aqueous based solution. By an "aqueous based solution" as used herein is meant a solution wherein more than 50% of the solvent is water, preferably more than 75%, and more preferably greater than 90% and most preferably, greater than 95%. The balance of solvent in the aqueous based solution is a non-interfering water miscible organic solvent. Typical water miscible organic solvents include alcohols having from 1 to 3 carbon atoms, polyols, such as ethylene or propylene glycol, or solvents such as glycerine, polyethylene glycols having a molecular weight ("MW") from 200–600, acetone, tetrahydrofuran (THF), dimethylsulfoxide (DMSO) and the like. Other water miscible organic solvents are well known to those of ordinary skill in the art.

The word "calibrator," as used herein, is meant to include any organic, inorganic, or organometallic compound that is capable of going into solution and that may be used to calibrate an assay for an analyte of interest. Preferably, the "calibrator" is the same as the analyte of interest or is an analog of the analyte of interest.

By the phrase "analyte of interest," as used herein, is meant a chemical compound or a biochemical composition that is to be measured. The analyte of interest is preferably a member of an immunologic pair. A "member of an immunologic pair" is one of two different molecules wherein one of the molecules has an area on its surface or a cavity which specifically binds to a particular spacial and polar organization of the other molecule. The members of the immunologic pair are referred to herein as a "ligand" and "antiligand." A "ligand" is an organic compound for which an antiligand naturally exists or can be prepared, e.g., hCG. An "antiligand" is any macromolecular compound, composition, or fragment thereof that is capable of recognizing (as manifested by an enhanced binding affinity to) a particular spatial and polar organization of a molecule, i.e., an epitopic or a determinant site. By way of example, antiligands include naturally occurring compounds, such as intrinsic factor, thyroxine-binding globulin, antibodies, enzymes, lectins and the like; and compounds prepared by human intervention, such as monoclonal antibodies, Fab or Fab' fragments, DNA probes, antisense strands of DNA and the like.

An "analog of the analyte of interest" is a compound that for purposes of the particular assay behaves substantially the same as the analyte of interest. Analogs of the analyte of interest are more commonly used when the analyte is a biochemical entity. For example, when the analyte is an antigenic material that has multiple epitopes, it may only be necessary to use a fragment of the analyte that contains the epitope(s) of interest. In the case of vitamin $B_{12}$, it is also well known in the art that analogs of vitamin $B_{12}$ will also bind to intrinsic factor, the antiligand for vitamin $B_{12}$. Similarly, analogs of folic acid are also known in the art to bind to beta-lactoglobulin. The substitution of an analog as a calibration material is well known to those of ordinary skill in the art.

In a particularly preferred embodiment of the present invention, the calibrator is not only the same compound or composition as the analyte of interest, it is also a member of an immunologic pair. U.S. Pat. No. 4,366,241 (Tom et al.) lists at columns 19–26 a variety of analytes that are members of an immunologic pair, including proteins, blood clotting factors, hormones, microorganisms, drugs, and vitamins, and is incorporated herein by reference. Any of these analytes are suitable for use as a calibrator in the composition of the present invention. However, preferred calibrators that are members of an immunologic pair include the following: human bone alkaline phosphatase antigen (HBAPAg); human chorionic gonadotropin (hCG); human leutenizing hormone (hLH); human follicle stimulating hormone (hFSH); creatine phosphokinase MB isoenzyme (CKMB); ferritin; carcinoembryonic antigen (CEA); prostate specific antigen (PSA); CA-549 (a breast cancer antigen); hepatitis B surface antigen (HBsAg); hepatitis B surface antibody (HBsAb); hepatitis B core antigen (HBcAg); hepatitis B core antibody (HBcAb); hepatitis A virus antibody; an antigen of human immunodeficiency virus HIV I, such as gp 120, p66, p41, p31, p24 or p17; the p41 antigen of HIV II; and the respective antiligand (preferably a monoclonal antibody) to any one of the above ligand calibrators. The HIV antigens are described more fully in U.S. Pat. No. 5,120,662 and in Gelderblood et al., Virology 156: 171–176 1987, both of which are incorporated herein by reference.

When the calibration material is a member of an immunologic pair, the calibrator solution is preferably a mammalian serum (such as human, porcine, bovine, murine, equine, sheep, goat, rabbit, rat, guinea pig, or a combination thereof) or a defined matrix or a combination or dilution thereof. A "defined matrix" is a proteinaceous solution of defined composition that stabilizes the calibrator or mimics one or more desirable properties of a mammalian serum.

By the phrase "working concentration range," as used herein, is meant the concentration range of the calibrators as is utilized in a particular assay. Thus, the working concentration range is assay dependent. Typically, the working concentration range encompasses the concentration range of the analyte of interest as found both in normal test samples and in abnormal test samples, i.e., samples that have concentrations of interest and that are reliably measured by the assay. For example, in a diagnostic test kit for the analyte insulin, the working concentration range for serum sample from a fasting patient includes both a normal concentration range and two abnormal concentration ranges that are of interest. The first abnormal concentration range is the subnormal range which reflects low insulin concentrations such as are associated with various forms of diabetes mellitus. The second abnormal concentration range is the supranormal range which reflects elevated insulin concentrations such as are associated with an insulinoma.

In yet other assays, such as for the enzyme prostatic acid phosphatase, the working concentration range may consist of only normal and elevated concentrations. The subnormal concentrations of the enzyme are not of clinical interest. In certain assays, the user or a physician may want to know how high is "high." In yet other assays, it is sufficient to know that the concentration of the analyte is elevated. An example of the latter is a diagnostic assay for human chorionic gonadotropin (hCG), wherein an elevated hCG is associated with pregnancy.

Thus, regardless of the analyte of interest, the "working concentration range" for the calibrator solution(s) is a concentration range that is tailored by the manufacturer in response to the concentration range of an analyte that is of interest to the end user.

By the term "marker," as used herein, is meant a chemical or physical agent that does not react with the calibration material but that is capable of producing a detectable signal in an amount or at a level that is directly related to the amount of marker in the solution. A preferred "marker" is a dye or a soluble metal ion or a complex thereof. A particularly preferred "marker" includes a dye bound to a protein carrier.

By way of example, an identifiable marker that is a physical agent is a particulate label such as the liposome sacs, erythrocyte ghosts, and dye coated polymers taught in U.S. Pat. No. 4,703,017 (Campbell) which is incorporated herein by reference. Dye coated polymers in the shape of microspheres are commercially available in a variety of colors, sizes, polymers, and surface groups, such as from Bangs Laboratories, Inc., Carmel, Ind. 46032. Although particulate sizes may vary depending upon the application, typical particle sizes are 5–500 nm.

When the marker is a soluble metal ion or its complex, the quantity of marker may be measured by any detection technique that is capable of quantitating a physical parameter of the ion or its complex that is proportional to the amount of ion or complex in solution. By way of example, suitable detection techniques include spectrophotometry, atomic absorption, flame photometry, or plasma emission or flame emission spectrometry. These techniques employ commercially available equipment and are well known to those of ordinary skill in the art.

By the term "dye," as used herein, is meant a compound or complex that absorbs light in the ultraviolet, visible or infrared spectrum, or that is phosphorescent, fluorescent, chemiluminescent, or a compound that either changes color (i.e., changes its absorption peak) or becomes colored in response to a pH change.

Dyes that absorb light in the visible region of the electromagnetic spectrum will give a calibrator solution a color. If a colored solution is undesirable, a colorless marker can be used. Colorless dyes absorb light in the ultraviolet or the infrared or change to a colored dye in response to a pH change. An example of the latter dye is phenolphthalein which changes from colorless to pink as a solution goes from acidic or neutral to alkaline (i.e., to a pH ranging from 8.3 to 10.0). A related dye is thymolphthalein which changes from colorless to blue as a solution goes from acidic or neutral to alkaline (i.e., to a pH ranging from 9.3 to 10.5). The chemical structures of both phenolphthalein and thymolphthalein are taught in "Fundamentals of Clinical Chemistry, "Tietz N. Ed, W. B. Saunders Co., Philadelphia, 1970 at p. 923 and 924, which are incorporated herein by reference.

A variety of other pH indicator dyes are well known to those of ordinary skill in the art, including those colored pH indicators that change to a second color in response to a pH change. Examples of the latter pH indicators, their respective pH range and color changes are as follows: bromocresol green, pH 3.8–5.4, yellow to green; bromophenol blue, pH 3.0–4.6, yellow to blue; bromothymol blue, pH 6.0–7.6, yellow to blue; congo red, pH 3.0–5.0, blue-violet to red; cresol red, pH 7.2–8.8, yellow to red; methyl orange, pH 3.0–4.4, red to yellow; methyl red, pH 4.2–6.3, red to yellow; phenol red, pH 6.8–8.4, yellow to red; thymol blue, pH 8.0–9.6, yellow to blue (acid form in 0.001N NaOH); and Toepfer's reagent, pH 2.9–4.0, red to yellow. The chemical structural formula for each of these indicators is taught in "Fundamentals of Clinical Chemistry, "Tietz N , W. B. Saunders Co., Philadelphia 1970 at pp. 920–924 which is incorporated herein by reference. Additional pH indicator dyes and their respective chemical structural formulas are taught in the 1989 Molecular Probes catalog at pages 92–94 which are incorporated herein by reference. (Molecular Probes, Eugene, Oreg.). It is also within the scope of the present invention to use the colored pH indicator dyes as markers in the absence of a pH change, such as a dye in a buffered solution.

To increase sensitivity, a marker with a high extinction coefficient is selected. Alternatively, a fluorescent or chemiluminescent molecule is utilized. To determine if a dilution testing method is feasible, a colored dye may be utilized in the initial tests.

A free dye in solution may change over time in its relative concentration and/or appearance. This can be attributed to a variety of factors including photobleaching, thermal decomposition, and/or physical absorption onto other materials (e.g., proteins) in the solution (i.e., matrix). However, the covalent coupling of the dye to a carrier protein helps to avoid or lower the effect of these problems. Covalent coupling also increases the stability of dyes that are susceptible to enzymatic degradation. The attachment of the dye to a carrier protein will also greatly lower the random association of the dye with other components in the serum or defined matrix, thus lowering assay variability. Preferably, the carrier protein would be present in the serum and/or defined matrix prior to attachment and would not be involved in the assay.

As an alternative to conjugating a dye to a carrier protein, one may utilize a colored protein as a marker in the present invention. Suitable colored proteins include the phycobiliproteins, which are fluorescent in addition to being colored. The phycobiliproteins include phycocyanin, allophycocyanin, B-phycoerythrin, R-phycoerythrin, and C-phycoerythrin. The phycobiliproteins are commercially available both in pure form, or as a variety of conjugates, such as from Molecular Probes, Inc., Eugene, Oreg.

Regardless of the type of marker that is used in the present invention, an identifiably effective but non-interfering amount of the marker should be employed. An amount of a marker in a stock calibrator solution is "non-interfering" if the amount of marker in a diluted calibrator solution, when analyzed as a test sample, does not exhibit a significant effect at the wavelength that is utilized in an assay for the analyte of interest. Typically, a marker is non-interfering if the marker's absorption and/or emission spectrum does not overlap with that of the signal producing system utilized in the assay.

Whether the amount of marker in a stock calibrator solution is "identifiably effective" is determined in accordance with a variety of factors including extinction coefficient, presence or absence of a carrier protein, absorption band width, location of the absorption band relative to any bands that are associated with the assay for the analyte of interest, thermal and photo-stability, non-specific binding, the solvent, and the composition and the pH of the solution. A person of ordinary skill in the art would readily determine and utilize an identifiably effective amount of the marker solution for the stock calibrator based upon the ability to reliably measure the amount of marker in the diluted (i.e., working) calibrator solution that is made from the stock calibrator solution and for which an accurate determination is sought. In so proceeding, the person of ordinary skill in the art would employ a relatively low amount of marker in the stock solution at first, subsequently increasing the amount of marker until an identifiably effective, but non-interfering amount is obtained. Markers that are determined to be either non-effective or effective but interfering are rejected. Another marker is then tested. Only those markers that are both identifiably effective and non-interfering are selected.

In the present invention, one or more markers are preferably bound to a protein (i.e., a carrier protein). A marker bound to a carrier protein is still referred to herein as a marker. A suitable carrier protein for use in the present invention is any non-interfering protein that is capable of binding one or more markers. Typical markers that are bound to a carrier protein include the dyes, metal ion complexes, and the phycobiliproteins. The preferred marker that is bound to a carrier protein is a dye.

The number of dye molecules that bind to a carrier protein is determined by a variety of factors including: the number of available binding sites that are present in the protein, the concentration of protein in the stock solution and the extinction coefficient of the dye. Binding a marker to a protein may be accomplished either directly, via a functional group, or indirectly via a functional group on a linker arm. The most common functional groups on a protein that are suitable for bonding to a marker are the sulfhydryl group (—SH) of cysteine; the $\epsilon$-amino group (—NH$_2$) of lysine; the carboxyl (—COOH) group of aspartic acid, glutumic acid or of C-terminal amino acids; the thioether (—S—CH$_3$) of methionine; the imidazolyl group of histidine; the guanidinyl group of arginine; the phenolic group of tyrosine; and the indolyl group of tryptophan. A listing of proteins, which would have one or more of those functional groups, is taught in U.S. Pat. No. 4,366,241 (Tom et al.) at cols. 19–20, all of which is incorporated herein by reference. The conjugation of chemical agents to proteins, via these functional groups, is taught, for example, in "Chemistry of Protein Conjugation and Cross-Linking," Wong, Shen, CRC Press, Boston, 1991, which is incorporated herein by reference. Of these functional groups, the amino groups and the sulfhydryl groups are preferred.

Not all proteins have free sulfhydryl groups. However, most protein do have free amino groups via the free amino group of lysine. Hence, as a general rule, conjugation of the marker to a protein, via its free amino groups, is preferred.

A preferred method for directly bonding a dye to the sulfhydryl group of a protein utilizes a dye having a maleimide moiety bound thereto. The maleimide moiety is specific for sulfhydryl groups and is capable of covalently binding the dye to the protein molecule. A variety of dyes that have a reactive maleimide bound thereto are commercially available, such as from Molecular Probes, Inc., Eugene, Ore. (e.g., Fluorescein-5-maleimide, Cat. No. F150; eosin-5-maleimide, Cat. No. E-118).

A preferred method for directly bonding a dye to an $\epsilon$-amino group on a protein utilizes a dye having an isothiocyanate functional group. The reaction between the isothiocyanate and the amino groups is pH dependent and occurs at an alkaline pH, preferably pH >8.5, wherein unprotonated amino groups are available for reaction. Dyes having isothiocyanate functional groups are commercially available, such as those from Molecular Probes, Inc. (e.g., tetramethylrhodamine-5-(and-6)-isothiocyanate, Cat. No. T-490; eosin-5-isothiocyanate, Cat. No. E-18; erythrosin-5-isothyiocyanate, Cat. No. E-332; and Malachite Green isothiocyanate, Cat. No. M-689). Those of ordinary skill in the art would recognize where to purchase or how to modify other dyes that would be suitable for use in the composition or methods of the present invention. See for example "Color Chemistry," Zollinger, Heinrich, VCH publishers, New York and Weinheim, (1987) which is incorporated herein by reference. Zollinger teaches the syntheses, properties and applications of organic dyes and pigments.

Any protein that is soluble in a stock solution of the present invention, that is non-interfering with the assay of interest, and that itself is not the analyte in the assay of interest is suitable for use as a carrier protein in the present invention. Preferred carrier proteins are the mammalian serum proteins, particularly where the assay is for a ligand or an antiligand. A number of mammalian proteins, which are suitable for use as carrier proteins, are taught in U.S. Pat. No. 4,366,241 (Tom) which is incorporated hereby reference.

In choosing a suitable carrier protein for a dye, one must consider a variety of factors relating to both the dye (such as extinction coefficient, hydrophobicity and size) and to the corresponding carrier protein (such as number and type of binding sites, and desirability of maintaining biological function and/or diffusion characteristics). To maintain some of the desired functions of a carrier protein in solution, it may be necessary to bind substantially less than the maximum number of dye molecules to the available binding sites. For example, the mammalian serum albumins are capable of functioning both as natural carrier proteins (e.g., unconjugated bilirubin, pharmaceuticals, etc.) and as agents maintaining normal colloidal osmotic pressure. The conjugation of a large number of dye molecules to albumin would alter its conformation and thus its ability to naturally function in either capacity.

Any ratio of dye to protein in the conjugate that gives rise to an identifiably effective amount of marker may be used in the present invention. In choosing the number of dye molecules to bind (i.e., conjugate) to a protein molecule, one would begin slowly at first by conjugating at least one dye molecule per protein molecule and then gradually increasing the number until one obtained a marker (albeit a conjugated marker) that is capable of being both identifiably effective and non-interfering. Thus, in some situations, the ratio of dye per protein molecule may be as low as 1:1, particularly when the dye has a high extinction coefficient and the protein molecule is small (e.g., molecular weight $\leq$ 10,000 daltons). In other situations, where the protein molecule is large (e.g., molecular weight > 69,000 daltons), a larger number of dye molecules (e.g., from 1-15+) per protein molecule are capable of being conjugated thereto. Carrier proteins of intermediate size would expectedly be capable of conjugating intermediate numbers of dye molecules per protein molecule. For purposes of this invention, a working ratio of dye molecules per protein molecule ranges from about 1:1 to about 15:1.

Preferred carrier proteins are the mammalian serum albumins, such as bovine serum albumin (BSA), human serum albumin, porcine serum albumin, sheep serum albumin, goat serum albumin, guinea pig serum albumin and the like, all of which are rich in lysine residues. For example, BSA has 59 lysine residues of which 30-35 have amino groups that are accessible for chemical coupling, such as via an isothiocyanate group. By way of example, a suitable carrier protein-dye conjugate (i.e., a marker) for use in the present invention is any one of the serum albumin-Malachite Green conjugates, preferably the bovine serum albumin-Malachite Green conjugate (i.e., the "BSA-Malachite Green conjugate"). Malachite Green is a triphenyl methane type dye that has two relatively sharp absorption bands at 629 nm and 427 nm. A preferred ratio of Malachite Green to BSA ranges from about 2.8:1 to about 7.0:1. The stability of the BSA-Malachite Green conjugate was found to be independent of the above dye to protein ratios (2.8 to 7.0).

From a measurement of the same physical parameter (e.g., absorption, emission, phosphorescence fluorescence, etc.) of a marker in both the stock and the diluted calibrator solutions, one is able to obtain the indirect, accurate and precise measurement of the amount of antigen (i.e., a calibrator) that is contained in any diluted calibrator solution. (See the Experimental Section herein.) The measurement of the physical parameter is both quick (approximately 30 minutes) and capable of providing a person, such as a diagnostic kit manufacturer, with an indirect but accurate analysis of a manufacturer's dilution process. By way of example, the Experimental Section herein teaches the synthesis of the marker BSA-Malachite Green.

When the marked stock solution of the present invention employs a visible dye as the marker, whether free or conjugated to a protein, it is capable of being converted into a series of diluted (i.e., working) calibrator solutions that span both a concentration range for the calibrator and a color range in proportion to the concentration of calibrator therein. Thus, in its second aspect, the present invention is directed to a diluted (i.e., working) calibrator solution that is both a member of a series of calibrator solutions and that contains therein a visible marker in proportion to the concentration of the calibrator therein. (As already defined herein, the word "calibrator" includes both a calibration material and a control material.)

In another aspect, the present invention is directed to a series of calibrator solutions that comprises a plurality of individual calibrator solutions, preferably 2-10 calibrator solutions, that span a range of predetermined calibrator concentrations wherein each solution in said series has a color intensity in proportion to the concentration of color therein. As discussed herein, the range of calibrator concentrations in any series is dependent upon a number of factors including the analyte of interest and the concentration range of interest that can be reliably measured by the assay.

A medical technologist performing a diagnostic assay that incorporates these calibration solutions would find useful the varying color intensity of each calibrator solution as a function of calibrator concentration. For example, prior to pipetting the calibrators in an assay, a technologist typically would align the calibrator solutions in an order of ascending or descending concentration, typically ascending. The corresponding ascent or descent in color intensity for the series of calibrator solutions so aligned provides the technologist with a quick visual assurance that the calibrator solutions are properly aligned for the pipetting step. Any break in the ascending or descending order of color intensity would indicate a mispositioned calibrator solution. After the pipetting step, the incrementally varying color of each calibrator solution is also capable of providing the technologist with a second visual assurance that the correct calibrator solution was pipetted, if at all, into the proper test tube or solution.

Thus, in another aspect, the present invention encompasses a method for performing a diagnostic assay that employs a series of calibrator solutions, the method comprising the steps of:
  aligning a series of calibrator solutions in an ascending or descending order based upon the concentration of a calibrator material contained therein, each calibrator solution in said series being characterized in that it contains a visible marker therein in proportion to the concentration of calibrator material contained therein; and
  viewing the color of the aligned series of calibrator solutions for non-reversing ascent or descent to assure that the calibrator solutions are in proper alignment for pipetting and/or sampling;
  whereby a reversal in the ascent or descent of the color in the aligned series of calibrator solutions would indicate misalignment.

On occasion, one or more calibrator solutions may be run in duplicate. Such duplicate calibrator solutions would have the same concentration of calibrator and therefore would have the same color. Placing the duplicate calibrator solutions in tandem series (i.e., side by side) would not result in a reversal of ascent or descent in color in the series of calibrators but merely a flat spot or break in the ascent or descent.

In its third aspect, the present invention is directed to a method that utilizes the intermediate composition (i.e., stock solution) of the present invention. The method of the present invention is for confirming that the correct dilution of a stock solution containing a calibration or control material ("calibrator") has been made, typically by a diagnostic kit or diagnostic component manufacturer. The method comprises the steps of:

a. combining an identifiably effective and a non-interfering amount of a marker and a predetermined quantity of a calibrator to form a marked stock calibrator solution having a first concentration of the marker and a second concentration of the calibrator;

b. calculating a proportion between the concentration of the marker and the concentration of the calibrator in the marked stock calibrator solution;

c. diluting the marked stock calibrator solution or a portion thereof by a predetermined amount to produce a diluted calibrator solution wherein the proportion is substantially maintained, the diluted calibrator having a first expected concentration of the marker that is associated with a first expected physical parameter and further having a second expected concentration of the calibrator therein;

d. measuring an actual physical parameter of the diluted calibrator solution, the actual physical parameter being proportional to the concentration of the marker therein;

e. comparing the actual physical parameter or a derivative thereof against the first expected physical parameter or a derivative thereof respectively to confirm that the diluting step was performed correctly.

In the above method, a predetermined quantity of a calibrator and a second predetermined quantity of a marker are combined in any order. Although the marker is referred to as "identifiable," it may be colorless when placed in the stock solution. The marker need only be capable of being identifiable or made identifiable at a later time. Identification may be visual or by instrumentation. Both the marker and the calibrator have their own respective concentrations in the marked stock calibrator solution. These concentrations may be the same or different.

The above method also includes the step of calculating a "proportion" between the concentration of marker and the concentration of the calibrator in the marked stock solution. By the word "proportion" or "proportional," as used herein, is meant a ratio or any relationship that is capable of being expressed mathematically, whether direct or inverse, linear or log. The "calculating" step, Step (b), may be performed at any time prior to or contemporaneous with the "comparing" step, Step (e) above.

The above method also includes the recited "diluting" step. Because the diluting step dilutes the marked stock solution that contains both the marker and the calibrator, the concentrations of both the marker and the calibrator are diluted equally. Accordingly, any proportion present in Step (a) is inherently maintained in Step (c). The expected concentrations of both the marker and the calibrator in any diluted solution are capable of being determined by using the formula:

$$\text{Conc}_i (\text{Volume}_i) = \text{Conc}_e (\text{Volume}_e)$$

wherein "$\text{Conc}_i$" is the initial concentration of marker in the marked stock calibrator solution; wherein "$\text{Volume}_i$" is the initial volume of the marked stock calibrator solution or portion thereof that was diluted; and wherein "$\text{Conc}_e$" and "$\text{Volume}_e$" are the expected concentration and the expected volume after dilution respectively. Because "$\text{Conc}_i$," "$\text{Volume}_i$" and "$\text{Volume}_e$" are known, one solves the equation for the expected concentration "$\text{Conc}_e$."

The "measuring" step limits the method of the present invention to measuring a physical parameter of the diluted solution that is associated with the actual concentration of the marker. The physical parameter chosen depends upon the marker and its physical properties of the marker. In the case of a dye, such concentration association physical parameters include absorbance, transmittance, fluorescence, phosphorescence, chemiluminescence, and the like. In the case of a metal ion or its complex, the concentration-associated physical parameters include absorption or emission of light at particular wavelengths. The word "proportional," as used in the measuring step, has already been defined above.

When the marker is eosin, the preferred concentration-associated physical parameter is phosphorescence or fluorescence. The eosin may be unconjugated, but preferably is conjugated to a carrier protein, such as via eosin-5-maleimide. Eosin-5-maleimide is commercially available, such as from Molecular Probes, Eugene, Oreg. Cat. No. E-118.

When the marker is fluorescein or rhodamine, the preferred concentration associated parameter is fluorescence. The fluorescein or rhodamine may be unconjugated, but preferably are conjugated to a carrier protein. Conjugatable fluorescein derivatives include fluorescein-r-maleimide and 5-(and-6)-carboxyfluorescein succinimidyl ester, such are commercially available from Molecular Probes, Eugene, Oreg. as Cat. Nos. F-150 and C-1311 respectively. Conjugatable rhodamine derivatives are commercially available, such as from Molecular Probes, Eugene, Oreg. as 5-(and-6-)-carboxytetramethyl rhodamine succinimidyl ester (Cat No. C-1171) and 5-(and 6-)-carboxy-X-rhodamine succinimidyl ester (Cat. No. C-1309).

When the marker is a colored protein, such as a phycobiliprotein, e.g., B-phycoerythrin, the concentration associated parameter may be absorbance or fluorescence. Because the protein is colored, it need not be conjugated to a dye. The phycobiliproteins, which have already been discussed herein, are commercially available, such as from Molecular Probes, Eugene, Oreg.

When the marker is the BSA-Malachite Green conjugate, the preferred concentration-associated physical parameter is absorbance. For this conjugate, the absorbance was measured at 628 nm using a Hewlett Packard 8451 A Diode Array Spectrophotometer. (The HP 8451 can only measure absorbance of even wavelengths). Its absorbance was observed to be linear over the range 0 to 1.5 absorbance units when plotted versus its concentration.

In the comparing step, the "actual physical parameter or derivative thereof" from Step (d) is compared to the corresponding "expected physical parameter or derivative thereof" from Step (c). For purposes of this invention, the step of comparing the actual physical parameter against the first expected physical parameter is meant to include any utilization of numbers that are derived from (i.e., derivatives thereof) the actual and expected physical parameters. For example, multiplying or dividing both the actual and expected absorbances of a diluted calibrator solution by some factor (e.g., 1000) would be comparing a derivative of the "actual physical parameter" to a derivative of the "expected physical parameter." A preferred derivative of the "actual physical parameter" is the "actual concentration." A preferred derivative of the "first expected physical parameter" is the "expected concentration."

Because of the relationship between the concentrations of marker and the calibrator in both the marked stock calibrator solution and the diluted calibrator solution, the present invention is also directed to a process for confirming the concentration of a calibration or control material ("calibrator") in a solution that has been diluted from stock. This method utilizes Steps (a)–(d) above. However, its final step, Step (e), comprises:

e. confirming that the actual concentration of calibrator in the diluted calibrator solution is substantially near its expected concentration by reference to a difference between the actual physical parameter and the first expected physical parameter or by reference, to a difference between derivatives thereof.

In performing the confirming step, a manufacturer would establish an acceptable difference (i.e., a tolerance) between the expected physical parameter and the actual (measured) physical parameter of the diluted calibrator solution. As already discussed above, mathematically manipulating the parameters to generate derivatives thereof, such as by multiplying or dividing, by one or more factors, is still considered within the scope of the invention. A particularly preferred derivative of the actual physical parameter that is measured in Step (d) is the actual concentration of the marker. A correspondingly preferred derivative of the first expected physical parameter is the "expected concentration."

Thus, the present invention provides compositions and methods that are useful to a diagnostic kit or component manufacturer and to the enduser of the kit or components as well.

EXPERIMENTAL PROCEDURES

A. Preparation of a BSA-Malachite Green Conjugate

Method

BSA powder (Bovine Fraction V, Sigma Chemical Co., St. Louis, Mo., Cat. No. 3294) was solubilized at 10 mg per ml in 0.05M borate buffer pH 9.5. Separately, 10 mg of Malachite Green isothiocyanate (Molecular Probes, Eugene, Oreg., Cat. No. M-689) was solubilized in 1 ml of DMSO. Eight equivalents of dye was added to the BSA solution and allowed to react for two hours. Using a piper, a small amount of the conjugate reaction was checked for completeness. Glass wool was placed in the base of the piper and then packed with 8 cm of G-25 Sephadex brand microbeads (MW cutoff 5,000) (Pharmacia, Piscathaway, N.J.). The column was then equilibrated with 0.1M phosphate buffer pH 7.0. Thereafter, 100 μl of the protein dye conjugate was placed on the column and eluted with 0.1M phosphate buffer pH 7.0. The first peak was collected and the coupling efficiency was determined using equations 1 through 5 below:

1) Molarity Malachite Green =

$$\frac{\text{Absorbance 629 nm}}{(\Sigma_{629\ nm}\ \text{Malachite Green}) \times (1\ \text{cm})}$$

2) Absorbance 280 nm Malachite Green =

$$\frac{(\text{Absorbance 629 nm}) \times (\Sigma_{280\ nm}\ \text{Malachite Green})}{(\Sigma_{629\ nm}\ \text{Malachite Green})}$$

3) Absorbance $BSA$ =
(Absorbance 280 nm − Absorbance 280 nm Malachite Green)

4) $BSA$ Conc. =
[(Absorbance 280 nm BSA/1.2 mg per ml)/66,000 MW)]

5) Dye/Protein = [(Molarity Malachite Green)/Molarity $BSA$)]

The reaction was allowed to continue until a ratio of five (5) dye molecules per protein molecule was obtained. The coupling reaction was quenched by neutralizing the solution using a saturated solution of tris[hydroxymethyl]aminomethane hydrochloride, i.e., "Trizma HCl" (e.g., Sigma Chemical Co., St. Louis, Mo., Cat. No. T 3253).

Results

On average, five Malachite Green molecules were attached per BSA molecule. BSA has 59 lysine residues of which 30–35 have amino groups that are accessible for chemical coupling. At pH 7, the ε-amino groups of lysine in a portion, such as BSA, are about 99% protonated and unreactive. However, above pH 8.5, a limited number of amines are unprotonated and reactive. At pH 9.5, as used above, the isothiocyanate group of the dye molecule reacted with the ε-amino group on the side chain of the amino acid lysine. Coupling reactions of this type, and under these conditions are approximately 60 percent complete after two hours. Therefore, eight equivalents of Malachite Green dye were added to the protein solution to obtain a 5 to 1 ratio of dye to BSA. The coupling of the dye to the BSA is observable as a wavelength shift of the dye. Using the 5:1 ratio of dye molecules/BSA molecule, it was possible to detect the absorbance of the BSA-Malachite Green conjugate at a 1:2500 dilution of a marked stock calibrator system that was approximately $4.4 \times 10^{-7}$M in the BSA-Malachite Green conjugate.

B. Purification of the BSA-Malachite Green Conjugate

Method

G-25 Sephadex was equilibrated with 0.1M phosphate buffer, pH 7.0. A 1.5 cm by 30 cm column was packed with the G-25 gel at a flow rate of 1 ml/min and monitored at 280 nm. The column was allowed to equilibrate with 0.1M phosphate pH 7.0 until a stable baseline was achieved. A solution of 1 mg per ml of BSA was prepared in 0.1M phosphate buffer pH 7.0. To lower non-specific binding, one void volume of the BSA solution was applied to the column and monitored at 280 nm. The column was washed with 0.1M phosphate buffer pH 7.0 until the original baseline was again obtained. Three ml of the BSA-Malachite Green conjugate solution was applied to the column. The conjugate was separated from the free dye and eluted using the 0.1M phosphate buffer pH 7.0 and monitored at 280 nm. The void protein-dye peak was collected, and using the previous stated equations, the dye (Malachite Green) to protein (BSA) ratios were determined. The BSA-Malachite Green conjugate peak was dialyzed (MW 12,000 cutoff) against water overnight at 4° C. and then lyophilized.

Void volume=$(2\pi r \times \text{column height}) \times (0.25)$**

** The "0.25" assumes that the G-25 spheres are in the closest pack arrangement such that the packed spheres will occupy 75 percent (0.75) of the total volume. In the equation, "r" is the radius of the column.

Results

The BSA-Malachite Green conjugate had a substantially larger molecular weight ( i.e., >66,000 daltons) than the molecular weight cutoff for the G-25 gel (5000 daltons). Accordingly, the conjugate was eluted off in the void volume. Prior to the separation (via elution), it was important to block the column with BSA to lower the non-specific absorption of the conjugate onto the gel. Due to the strong color, a determination of separation between the free dye and the conjugate dye would be extremely difficult if nonspecific interactions were taking place. The column did turn a slight shade of blue indicating that not all the undesirable interactions had been eliminated. Two blue bands were monitored at 280 nm. A majority of the color was located in the void peak. The conjugate was dialyzed to remove the phosphate buffer and any dye non-specifically bound to the protein.

C. Preparation of a Marked Stock Calibrator Solution Containing a BSA-Malachite Green Conjugate and Hypothetically Containing 5000 ng/ml of a Calibrator of Interest Method To determine the feasibility of using an marker in a stock calibrator solution for confirming the accuracy of dilutions therefrom, a marked stock solution that contained BSA-Malachite Green conjugate as its marker and that hypothetically contained 5,000 ng/ml of a calibrator was prepared as follows. To a 5.0 ml volumetric flask was added about 2.5 ml of deionized water. Thereafter, the following reagents were added sequentially: 12.4 mg citric acid (monohydrate), 77.7 mg sodium phosphate dibasic (anhydrous), 6.7 mg D-mannitol, 6.7 mg sodium azide, 6.7 microliters of the non-ionic detergent "Nonidet-P40" (Sigma Chemical Co., St. Louis, Mo., Cat. No. N6507), 0.836 ml of 30% bovine serum albumin (Intergen Co., Purchase, N.Y.), and 410 mg BSA-Malachite Green conjugate, such as from Section B above. Between the addition of each reagent, the solution was mixed sufficiently until all solids were dissolved. After the additions of the BSA and the Nonidet respectively, the solution was mixed for five minutes. The mixing must be vigorous enough to cause a vortex but not so vigorous as to cause foaming. The pH was then adjusted to fall within the range of 6.9 to 7.1 with either 0.1N NaOH for pH <6.9 or 0.1N HCl for pH >7.1. Once the pH was in the specified range, sufficient sodium azide was added to provide a 0.02% concentration when diluted to 5.0 ml. The solution was then mixed until all of the solids were dissolved. Sufficient deionized water was added to the solution to bring the volume up to the 5.0 ml mark. The resulting marked solution was designated as a marked stock calibrator solution that hypothetically contained 5000 ng/ml of a calibrator (e.g., an antigen) of interest. The marked stock solution was stored in the dark at 4° C.

D. Preparation of Working Solutions; Taking Absorbances

1. Preparation Of A Defined Matrix

A defined matrix for use in diluting a marked stock solution was prepared in proportion to the following procedure. To a 1000 ml volumetric flask having 500 ml of deionized water therein is added 11.6 g of anhydrous sodium phosphate dibasic. The contents are then mixed until all of the solids are dissolved. Thereafter, 1.86 g of citric acid monohydrate is added to the solution and the contents are mixed until all solids are dissolved. Next, 333.3 ml of 30% bovine serum albumin (BSA) is added to the flask and the contents are stirred for at least five minutes. The stirring must be sufficient to form a vortex but not so vigorous as to cause foaming. To the solution is then added 1.0 g of a carbohydrate, e.g., mannitol, and the solution is stirred until all of the solids are dissolved. Thereafter, one ml. of non-ionic detergent, e.g., Nonidet P-40, is added to the solution. Stirring is continued for 5 minutes as described above. The pH is then adjusted so that it falls within the range from 6.9 to 7.1 using either 10N sodium hydroxide for pH less than 6.9 or 6N hydrochloric acid for pH greater than 7.1. Once the pH is in the specified range, 1.0 g of sodium azide is added to the solution which is then mixed until all of the solids are dissolved. Finally, sufficient deionized water is added to the flask to bring the solution up to the 1000 ml mark. After filtration through a 0.2 micron filter, the resulting solution is a defined matrix that is ready for use.

2. Dilution Of The Marked Stock Calibrator Solution With Defined Matrix

The marked stock solution of Section C (that corresponded to 5000 ng/ml of an antigenic calibrator), was diluted with defined matrix (Section D(1) above) to prepare a series of diluted calibrator solutions (i.e., "working calibrator solutions"). The diluted calibrator solutions were equivalent to 2.0, 5.0, 10.0, 25, and 50.0 ng/ml of antigen. In order to achieve these levels, the marked stock solution was diluted 1:2500, 1:2000, 1:1000, 1:500, and 1:100 respectively. The absorbance for each of these diluted calibrator solutions was determined. The samples at each level were then divided into two sets of three. One set was placed in the dark. The other set was placed in the room light. Both samples sets were stored at room temperature. The absorbance of each of the samples was read on a Hewlett Packard 8451A diode array spectrophotometer on days 1, 2, and 6 after preparation. The percent coefficient of variation (% CV) for each of the samples was calculated using equations 1-3 below:

1) $\text{Percent Error} = \frac{\text{Reading Difference (Absorbance)}}{\text{Average}}$ 2) $\text{Standard deviation} = [\text{Sum of (mean-value)}^2/N]^{\frac{1}{2}}$
   where $N$ = number of values 3) $\text{Percent C.V.} = \frac{\text{Standard Deviation} \times 100}{N}$ Results The difference in the absorbance, percent error, and coefficient of variation ("CV") between light and dark samples were determined. The percent CV's were good over the range in which the measurements were made. However, at the lower concentrations (larger dilution) the signal to noise ratio had increased. The fluctuation in the readings was due to the spectrophotometer having a precision of ±0.016 absorbance units. On each of days 1, 2, and 6, the CV's were lower than five percent.

The calibration curves for each of the individual days (1, 2, and 6) were all linear with correlation coefficients of 1. The intercept and slope for the calculated line for the data points change slightly. This can be attributed to the day to day variations in the spectrophotometer and can be observed when all three days are plotted on the same graph. The bar graphs for day 2 and intra-assay CV's indicate that there was no significant difference ( i.e.,<0.03 absorbance units) between the light and dark sample sets. The deviation in the absorbance readings was due to the fluctuation in the spectrophotometer and can be observed in the readings at the 0.0 ng/ml sample. Any difference in absorbance that is equal to or less than the 0.0 ng/ml value was due to the spectrophotometer. The intra-assay CV's did however increase slightly on day 6, but were still below 5%. The inter-assay CV's were larger at the lower concentrations but were below 5%.

E. Dilution Measurements Using a Flow Through Cell

Method

The marked stock solution of Section C herein was diluted 1:4000, 1:2000, and 1:1000 to correspond to diluted calibrator solutions of 1.25, 2.50, and 5.00 ng/ml of antigen respectively. Five samples at each concentration (0.0, 1.25, 2.50, and 5.00 ng/ml) were injected using the BioRad Model AS-100 HRLC automatic sampling system into ABI, Analytical Kratos Division, Spectroflow 783 spectrophotometer at a flow rate 1 ml per minute and monitored via their respective absorbances at 629 nm.

Results

The flow through cell was more precise in the absorbance measurements for the dilution of the stock standard in comparison to measurements made on the Hewlett Packard ("HP") 8451A spectrophotometer. The intra-assay CV's were all lower than 0.4%. This is equal to a 10 fold increase in precision over the results obtained with the HP instrument. The data when plotted again, as with the HP system, was a straight line with a correlation coefficient of one. In the present measurements, the area was plotted as a function of dilution, whereas with the data from the HP, the absorbance was plotted as a function of calibrator (antigen) concentration.

F. pH vs. Absorbance for the BSA-Malachite Green Conjugate

Method

The effect of pH on the absorbance spectrum of the BSA-Malachite Green conjugate was monitored at 629 nm. A series of BSA Malachite Green conjugate solutions ($5.5 \times 10^{-7}$M) were prepared in carbonate buffer that was adjusted to pH 3.2, 5.2, 6.2, 7.2, and 9.2. Using a Beckman DU 70 spectrophotometer, the absorbance spectrum (250 nm to 700 nm) for each conjugate solution was monitored.

Results

The spectrum for the protein conjugate showed three absorbance bands (280, 500, and 629 nm). The bands at 500 nm and 629 nm are due to the Malachite Green and at 280 nm is a result of the aromatic amino acids in the protein. The dye absorbs stronger at 629 nm under acidic conditions (pH 3.2) when compared to basic conditions (pH 9.2). The effect of pH becomes more pronounced at the more acidic solutions.

G. Validation of the Dilution Method

Aliquots of the marked stock calibrator solution from Section C above were diluted 1,5000, 1:2000, 1:1000, and 1:4000 with the defined matrix from Section D(1) above. These dilutions correspond to working solutions having 1.0, 2.5, 5.0, and 12.5 ng/ml of calibrator respectively. At each concentration, the working solution was divided into thirds. The first third was placed into 1.5 ml samples and frozen at −20° C. for later use as a series of control The second third was placed in the dark at 5° C. The last third was placed at 5° C. but in room light. The absorbance of the samples stored 5° C. were read at 629 nm at one week intervals. Standard curves (i.e., calibration curves) were constructed for each week. The frozen samples were thawed and read as controls at one week intervals. Using the calibration curves from the 5° C. samples, the concentration of hypothetical antigen in the frozen samples were calculated.

Results

The calibration curves for all samples (light and dark) were linear (correlation coefficient=1) over the 40 day period in which these experiments were performed. The variation (0.010–1.900) for the % CV's between the light and dark readings fluctuated from week to week. The highest % CVs (e.g., 1.900) were observed in the blank sample (containing no dye). This was probably a result of the noise in the UV lamp. When the data is plotted, there appears to be no trend in the graphs to suggest that the light and dark samples were drifting from one another. It does suggest however, that fluctuation was consistent within a week.

The calibration curves were able to consistently determine the correct concentration of the frozen samples within the experimental error for the week. Plotting the calculated values as a function of the assay date results in three straight horizontal lines. The three lines confirm graphically the dye conjugate's ability to determine dilution. The fact that the lines are horizontal suggests that the dye that is stored in solution at 5° C. is the same as the dye that is stored frozen. The inter-assay CV's for the readings on each day were all below 1.2 percent.

H. Proposed Method for Dilution Determination for a Series of Working Calibrator Solutions Using the procedure of Section A above, five Malachite Green (dye) molecules are coupled per BSA (protein) molecule. The resulting BSA-Malachite Green conjugate is purified on G-25 Sephadex as described in Section B. The purified BSA-Malachite Green conjugate is then be added in sufficient amount to a stock solution of calibrator on known concentration to produce a marked stock solution that is capable of providing an absorbance reading of 0.1 absorbance units for its diluted calibrator solution at the highest dilution. Also, unconjugated BSA is added in accordance with Section C above to the defined matrix defined above. An adequate amount of the marked stock calibrator solution is then removed for the construction of standard curves before proceeding to manufacturing. The kit calibrators are then diluted with defined matrix (containing no dye) as in manufacturing to achieve the desired antigen concentrations (i.e. 2, 10, 25, 50, and 100 ng/ml for PSA). The diluted calibrator solutions are then aliquoted (2 ml) into vials for storage (−20° C.). The aliquots are thawed and read, as needed, to construct the desired standard curves for testing subsequent manufacturing lots.

I. Identification and Adjustment of an Errant Calibrator Solution

1. Preparation Of A Pre-Stock Solution Containing 5000 ng/ml of Human Bone Alkaline Phosphatase Antigen The antigen cell line, SAOS-2 Osteogenic Sarcoma primary, human type (ATCC Cat. No. HTB 85), was cultured for eleven days in HP Pro Media (Irvine, Calif.) to which was added 5 mg/L human recombinant insulin (Nucellin-Na). At eleven days, a membrane fraction was prepared from the cells and the alkaline phosphatase activity of the harvested membrane fraction was determined. Alkaline phosphatase antigen was extracted from the membrane fraction enzymatically, e.g., with a solution of phospholipase C (B. Cereus Company), pH 7.5, the extraction solution having one unit of phospholipase C activity for every 10 units of alkaline phosphatase activity in the membrane fraction. The concentration of human alkaline phosphatase antigen in the extract was about 100,000 ng/ml. A sufficient quantity (i.e., volume) of the quantitated and purified extract was placed in an appropriately sized flask such that upon dilution of the extract volume to the mark, a solution containing 5000 ng/ml of alkaline phosphatase antigen would be produced. This flask containing the undiluted volume purified extract is referred to herein as a "pre-stock" solution of human bone alkaline phosphatase.

2. Preparation Of A Marked Stock Solution Containing 5000 ng/ml Of Human Bone Alkaline Phosphatase Antigen To the pre-stock solution from Section I(1) above was added sufficient BSA-Malachite Green conjugate, such as purified in Section B (i.e., 5:1 dye to protein ratio), to provide a marked stock calibrator solution, which upon dilution in the volumetric flask to the mark with defined matrix from Section D(1), had an absorbance of approximately 50 absorbance units at 629 nm. The absorbance of the marked stock calibrator solution was intentionally set to approximately 50 absorbance units so that the most dilute calibrator solution (15 ng/ml) (i.e., a 1:333 dilution) would have an absorbance of approximately 0.15 absorbance units.

The marked stock calibrator solution was then diluted with a defined matrix to produce a series of diluted calibrator solutions having concentrations of 0, 15, 30, 45, 60 and 120 ng/ml respectively. However, in the above series, the 45 ng/ml calibrator was intentionally made incorrectly, i.e., approximately 10 percent high. The absorbances of the diluted calibrator solutions were then measured at 629 nm and plotted versus the concentration. The calibrators that were prepared properly diluted linearly when plotted as absorbance at 629 nm versus concentration. Based upon the difference between its expected absorbance and its measured absorbance, a portion of the 45 ng/ml calibration solution was adjusted by the addition of defined matrix and re-read on the spectrophotometer. All diluted calibrator solutions, including the incorrect and adjusted 45 ng/ml calibrator, were analyzed for bone alkaline phosphatase antigen using Hybritech's Tandem ® Ostase ™ Assay (Hybritech, San Diego, Calif.).

Results

The calibrators that were prepared correctly diluted linearly (absorbance at 629 nm vs. human bone alkaline phosphatase Ostase antigen Concentration). The corresponding Tandem Ostase assay also diluted linearly (counts per minute vs. Ostase antigen Concentration). The CV's for the Tandem Ostase assay range on average from 2% to 3% and were within the specifications set for the Ostase assay. The addition of defined matrix to the incorrectly prepared 45 ng/ml calibrator was able to adjust the absorbance of the calibrator at 629 nm to the correct value. The Tandem Ostase assay was also able to detect the incorrectly prepared calibrator. The Tandem Ostase assay also reflected the adjustment made on the incorrectly prepared 45 ng/ml. The concentration of the antigen in the calibrators obtained from the Tandem Ostase assay correlated strongly (correlation coefficient=0.996) with the results from the dye absorbance experiments. However, there was a slight constant bias towards the dye data. This is probably the result of an incorrect value assigned to the 5000 ng/ml marked stock calibrator solution after the addition of the conjugate.

Conclusion

The measurement of a physical parameter (e.g., absorbance) that is associated with the marker in the diluted calibrator solutions was able to detect the correct and incorrectly diluted calibrator solutions. The marker also detected the proper adjustment of the 45 ng/ml calibrator to the correct concentration. The time required for the adjustment was minimal in comparison to the approximately three days required for the Tandem Ostase assay. The strong correlation between the method of the present invention and the data from the Tandem assay suggests that the dye had no effect on the performance of the Ostase assay.

J. Preparation of a Marked Stock Solution Containing 5000 ng/ml Human Alkaline Phosphatase Antigen as the Calibrator and B-Phycoerythrin as the Marker To a 1000 ml volumetric flask is added a sufficient volume of purified extract from Section I(1) to provide 5000 ng of human bone alkaline phosphatase antigen. The defined matrix from Section D(1) is added to the flask to bring the volume to about the 900 ml mark. The contents are mixed by stirring without creating a vortex. To the flask in then added 2.4 mg of B-phycoerythrin, mol. wt.=240,000 daltons. (Molecular Probes, Inc., Eugene, Oreg., Cat No. P-800). The contents are again mixed by stirring for a minimum of 15 minutes without foaming. Thereafter, the flask is diluted to the 1000 ml mark with defined matrix and stirred for about ten minutes without creating a vortex. The resulting marked stock calibrator solution contains 5000 ng/ml of human bone alkaline phosphatase antigen and is $1 \times 10^{-8}$M in B-phycoerythrin. B-phycoerythrin is a fluorescent dye that absorbs at 545 nm and emits at 575 nm.

Preparation of Working Calibrator Solutions of Human Bone Alkaline Phosphatase Antigen Marked with B-Phycoerythrin The marked stock solution from Section J (that corresponded to 5000 ng/ml of human bone alkaline phosphatase antigen, "HBAPAg" is diluted with defined matrix from section D(1) to prepare a series of diluted calibrator solutions, i.e., "working calibrator solutions." The diluted calibrator solutions contain 15, 30, 45, 60 and 120 ng/ml of the calibrator, HBAPAg. In order to achieve these calibrator concentrations, the marked stock calibrator solution is diluted with defined matrix as follows: 1:333; 1:167; 1:111; 1:83 and 1:41.7, respectively. An aliquot of the defined matrix is used as the 0 ng/ml calibrator.

Preparation of a Marked Stock Calibrator Solution Containing 5000 ng/ml of Prostate Specific Antigen as Calibrator and Phenolphthalein-HSA Conjugate as the Marker 1. Preparation Of Phenolphthalein-N-Hydroxy-2-Sulfosuccinimidyl Ester The above identified phenolphthalein ester is prepared by adding one equivalent of N-hydroxysulfosuccinimide (Pierce Chemical Co., Rockford, Ill.) to phenolphthalein, with a slight excess of dicyclohexylcarbodiimide in dry DMF, and mixing overnight. The mixture is cooled at 4° C. for three hours to allow the urea side product to precipitate out of solution. The urea is removed by filtration on a Whatman #2 filter paper and the filtrate is collected. The ester is precipitated by the addition of 20 volumes of ethyl acetate to the filtrate. The phenolphthalein ester is collected and stored under nitrogen. See:
(1) Yip, C.; Yeung, C.; Moule, M. *J. Biol. Chem.* 1978, 253 (6), 1743–5; and
(2) Anderson, G.; Callahan, F.; Zimmerman, J. *J. Am. Chem. Soc.* 1967, 89 (1).

2. Conjugation Of Phenolphthalein To Human Serum Albumin ("HSA")

Human serum albumin is solubilized at 10 mg/ml in 0.1M phosphate buffer, pH 7.8. A fifteen-fold molar excess of phenolphthalein sulfosuccinimidyl ester from L(1) above is added to the above described solution of human serum albumin with gentle stirring and allowed to react for thirty minutes. The resulting reaction mixture is then passed over a G-25 size exclusion column as described in Section B and eluted with 0.1M phosphate buffer pH 7.0. The eluent is monitored at 280 nm. The first peak, which contains the conjugate, is collected. A portion of the eluent is made basic and the absorbance of the phenol-phthalein is measured at 550 nm. The phenolphthalein-HSA ratio of the conjugate is determined utilizing the equations in Section A above. The remainder of the phenolphthalein-HSA conjugate peak is dialyzed (MW 12,000 cutoff) against water overnight at 4° C. and then lyophilized.

3. Preparation Of A Pre-Stock Calibrator Solution Of Human Prostate Specific Antigen Human prostate specific antigen is a single chain glycoprotein with a molecular weight of approximately 34,000 daltons, containing 7% carbohydrate by weight. Wang et al., "Purification of a Human Prostate Specific Antigen," Invest. Urol. 17:159 (1979). Human prostate specific antigen ("PSA") is obtained in purified form according to the process disclosed in U.S. Pat. No. 4,446,122 (Chu). The purified extracts are concentrated according to Chu until one obtains a pre-stock calibrator solution having a concentration of PSA in slight excess of 10,000 ng/ml. Based upon the concentration of PSA in the purified extract, one is able to calculate the amount of extract that is to be transferred to a volumetric flask, which when diluted to volume with defined matrix, such as in Section (D)(1), would provide a stock calibrator solution having a concentration of 5000 ng/ml of PSA. This undiluted volumetric flask containing the appropriate amount of purified extract of PSA is referred to as a pre-stock solution.

4. Preparation Of A Marked Stock Calibrator Solution Containing HSA-Phenolphthalein Conjugate As The Marker And PSA As The Calibrator To the pre-stock PSA calibrator solution from Section K(3) above is added a sufficient amount of lyophilized phenolphthalein-HSA conjugate, such as prepared in Section K(2) above, and defined matrix, such as prepared in Section (D)(1), to provide a marked stock calibrator solution having 5,000 ng/ml PSA and containing $1.885 \times 10^{-3}$ MHSA-phenolphthalein conjugate. (A defined matrix in which HSA is substituted for BSA may also be used in the dilution.) A 2 ng/ml working calibrator that is prepared by diluting such a 5000 ng/ml marked stock calibrator solution is expected to have a spectroscopic absorbance of approximately 0.1 absorbance units at 550 nm in a basic media, pH 10.

What is claimed is:

1. A composition for facilitating a determination that a stock solution containing a calibration or control material ("calibrator") dissolved therein has been diluted correctly, said composition comprising, a solution having dissolved therein:
   a) a first compound ("calibrator") designated for use in calibrating an assay for an analyte of interest over a working concentration range, said calibrator being the same or substantially the same as the analyte of interest, said calibrator being present in said solution at a concentration that is substantially above the working concentration range of said analyte of interest; and
   b) an identifiably effective and non-interfering amount of a second compound ("marker") dissolved therein substantially for identifying the dilution level of said stock solution over the working concentration range of said calibrator, said marker being a dye conjugated to a carrier protein, said marker having a concentration that is proportional to the concentration of said calibrator, said marker neither participating as a reactant nor as a label on a reactant in said assay for said analyte of interest.

2. The composition of claim 1 wherein the stock solution is an aqueous based solution.

3. The composition of claim 1 wherein the calibrator is a ligand or an antiligand.

4. The composition of claim 3 wherein the ratio of dye to carrier protein is within the range of about 1:1 to about 15:1.

5. The composition of claim 4 wherein the carrier protein is a mammalian serum protein.

6. The composition of claim 5 wherein the mammalian serum protein is selected from the group consisting of bovine serum albumin, human serum albumin, porcine serum albumin, sheep serum albumin, murine serum albumin, goat serum albumin, and guinea pig serum albumin.

7. The composition of claim 6 wherein the mammalian serum protein is bovine serum albumin.

8. The composition of claim 7 wherein the dye absorbs light in the visible spectrum.

9. The composition of claim 8 wherein the calibrator is selected from the group consisting of prostate specific antigen, human bone alkaline phosphatase antigen, human chorionic gonadotropin, follicle stimulating hormone, human leutenizing hormone, creatine phosphokinase MB isoenzyme, ferritin, carcinoembryonic antigen, CA-549, hepatitis B surface antigen, hepatitis B surface antibody, hepatitis B core antigen, hepatitis B core antibody, hepatitis A virus antibody, hepatitis C virus antibody, the p41 antigen of HIV II, the gp120 antigen of HIV I, the p66 antigen of HIV I, the p41 antigen of HIV I, the p31 antigen of HIV I, the p24 antigen of HIV I, the p17 antigen of HIV I, and an antiligand to any one of said aforementioned antigens.

10. The composition of claims 1 or 8 wherein the dye is selected from the group consisting of Malachite Green, fluorescein, eosin, tetramethylrhodamine, phenolphthalein and erythrosin.

11. The composition of claim 10 wherein the dye is Malachite Green.

12. The composition of claim 11 wherein the ratio of dye to carrier protein is within the range from about 2.8:1 to about 7:1.

13. A series of calibrator solutions, each calibrator solution in said series having therein a predetermined concentration of a non-visible calibrator and an identifiably effective and non-interfering amount of a visible marker, said marker being a colored dye conjugated to a carrier protein, the amount of visible marker in each calibrator solution being proportional to the concentration of said calibrator, said series of calibrator solutions spanning a predetermined range of calibrator concentrations and a corresponding range of marker concentrations, whereby each solution in said series of calibrator solutions has a color intensity in proportion to the concentration of calibrator therein.

14. The series of calibrator solutions of claim 13 wherein the calibrator is a ligand or an antiligand.

15. The series of calibrator solutions of claim 14 containing from 2 to 10 calibrator solutions.

16. The series of calibrator solutions of claim 15 wherein one or more calibrator solutions in said series are capable of functioning as control solutions in an assay.

17. The calibrator solution of claims 13 or 16 wherein the calibrator is selected from the group consisting of human bone alkaline phosphatase antigen, human chorionic gonadotropin, human leutenizing hormone, human follicle stimulating hormone, ferritin, carcinoembryonic antigen, prostate specific antigen, CA-549, creatine kinase MB isoenzyme, hepatitis B surface antigen, hepatitis B surface antibody, hepatitis B core antigen, hepatitis B core antibody, hepatitis A virus antibody; hepatitis C virus antibody, the p41 antigen of HIV II, the gp120 antigen of HIV I, the p66 antigen of HIV I, the p41 antigen of HIV I, the p31 antigen of HIV I, the p24 antigen of HIV I, the p17 antigen of HIV I, and an antiligand to any one of said aforementioned antigens.

18. The series of calibrator solutions of claim 16 wherein the colored dye is selected from the group consisting of Malachite Green, eosin and erythrosin.

19. The series of calibrator solutions of claim 18 wherein the carrier protein is a mammalian serum protein.

20. The series of calibrator solutions of claim 19 wherein the mammalian serum protein is a mammalian serum albumin.

21. The series of calibrator solutions of claim 20 wherein the mammalian serum albumin is selected from the group consisting of bovine serum albumin, human serum albumin, procine serum albumin, sheep serum albumin, murine serum albumin, goat serum albumin and guinea pig serum albumin.

22. The series of calibrator solutions of claim 21 wherein the mammalian serum albumin is bovine serum albumin.

23. The series of calibrator solutions of claim 22 wherein the colored dye is Malachite Green.

24. The series of calibrator solutions of claim 23 wherein the ratio of dye to protein is within the range from about 2.8:1 to about 7:1.

25. A series of calibrator solutions for calibrating a diagnostic test kit, said series spanning a predetermined range of calibrator concentrations, each solution in said series having a predetermined concentration of calibrator therein and a second predetermined and non-interfering concentration of a colored marker therein, said marker being a colored dye conjugated to a carrier protein, said concentration of colored marker in each solution in said series being proportional to the concentration of calibrator therein, each solution in said series having a color intensity in proportion to the concentration of calibrator therein such that said series spans a range of color intensity in proportion to the range of calibrator concentrations therein.

26. The series of calibrator solutions of claim 25 wherein said working calibrator solutions are aqueous based.

27. The series of calibrator solutions of claim 26 wherein the calibrator is a ligand or an antiligand.

28. The series of calibrator solutions of claim 27 wherein the ratio of dye to carrier protein is within the range from about 1:1 to about 15:1.

29. The series of calibrator solutions of claim 28 wherein the carrier protein is a mammalian serum protein.

30. The series of calibrator solutions of claim 29 wherein the mammalian serum protein is selected from the group consisting of bovine serum albumin, human serum albumin, porcine serum albumin, sheep serum albumin, murine serum albumin, goat serum albumin, and guinea pig serum albumin.

31. The series of calibrator solutions of claims 23 or 25 wherein the calibrator is selected from the group consisting of prostate specific antigen, human bone alkaline phosphatase antigen, human chorionic gonadotropin, follicle stimulating hormone, leutenizing hormone, creatine phosphokinase MB isoenzyme, ferritin, carcinoembryonic antigen, CA-549, hepatitis B surface antigen, hepatitis B surface antibody, hepatitis B core antigen, hepatitis B core antibody, hepatitis A virus antibody, hepatitis C virus antibody, the p41 antigen of HIV II, the gp120 antigen of HIV I, the p66 antigen of HIV I, the p41 antigen of HIV I, the p31 antigen of HIV I, the p24 antigen of HIV I, the p17 antigen of HIV I and an antiligand to any one of said aforementioned antigens.

32. The series of calibrator solutions of claim 30 wherein the mammalian serum protein is bovine serum albumin.

33. The series of calibrator solutions of claims 32 or 29 wherein the dye is selected from the group consisting of Malachite Green, fluorescein, eosin, phenolphthalein, tetramethylrhodamine, and erythrosin.

34. The series of calibrator solutions of claim 33 wherein the dye is Malachite Green.

35. The series of calibrator solutions of claim 34 wherein the ratio of dye to protein is within the range from about 2.8:1 to about 7:1.

36. A method for performing a diagnostic assay for an analyte of interest, the method comprising the steps of:
  a. providing a series of calibrator solutions spanning a predetermined range of calibrator concentrations, each solution in said series having a predetermined concentration of calibrator therein, said calibrator being the same or substantially the same as the analyte of interest;
  b. aligning the series of calibrator solutions in an ascending or descending order based upon the concentration of a calibrator material contained therein, each calibrator solution in said series being characterized in that it further contains a visible and non-interfering marker therein in proportion to the concentration of calibrator material contained therein, said marker being a colored dye conjugated to a carrier protein;
  c. viewing the color of the aligned series of calibrator solutions for non-reversing ascent or descent to assure that the calibrator solutions are in proper alignment for pipetting and/or sampling;
  whereby a reversal in the ascent or descent of the color in the aligned series of calibrator solutions would indicate misalignment in the assay; and d. performing a diagnostic assay using said series of calibrator solutions.

37. A process for confirming the correct dilution of a stock solution containing a calibration or control material ("calibrator") comprising the steps of:
   a. combining an identifiably effective and non-interfering amount of a marker and a predetermined quantity of a calibrator to form a marked stock calibrator solution having a first concentration of said marker and a second concentration of said calibrator, said marker being a dye conjugated to a carrier protein;
   b. calculating a proportion between the concentration of the marker and the concentration of the calibrator in the marked stock calibrator solution;
   c. diluting the marked stock calibrator solution or a portion thereof by a predetermined amount to produce a diluted calibrator solution wherein said proportion is substantially maintained, said diluted calibrator solution having a first expected concentration of said marker that is associated with a first expected physical parameter and further having a second expected concentration of said calibrator therein;
   d. measuring an actual physical parameter of the diluted calibrator solution, the actual physical parameter being proportional to the actual concentration of the marker therein;
   e. comparing the actual physical parameter or a derivative thereof to the first expected physical parameter or a derivative thereof respectively to confirm that the diluting step was performed correctly.

38. The process of claim 37 wherein the marked stock calibrator solution is an aqueous based solution.

39. The process of claim 38 wherein the calibrator is a ligand or an antiligand.

40. The process of claim 39 wherein the ratio of dye to carrier protein is within the range from about 1:1 to about 15:1.

41. The process of claim 40 wherein the carrier protein is a mammalian serum protein.

42. The process of claim 41 wherein the mammalian serum protein is selected from the group consisting of bovine serum albumin, human serum albumin, porcine serum albumin, sheep serum albumin, murine serum albumin, goat serum albumin, and guinea pig serum albumin.

43. The process of claims 39 or 42 wherein the calibrator is selected from the group consisting of prostate specific antigen, human bone alkaline phosphatase antigen, human chorionic gonadotropin, follicle stimulating hormone, human leutenizing hormone, creatine phosphokinase MB isoenzyme, ferritin, carcinoembryonic antigen, CA-549, hepatitis B surface antigen, hepatitis B surface antibody, hepatitis B core antigen, hepatitis B core antibody, hepatitis A virus antibody, hepatitis C virus antibody, the p41 antigen of HIV II, the gp120 antigen of HIV I, the p66 antigen of HIV I, the p41 antigen of HIV I, the p31 antigen, the p24 antigen of HIV I, the p17 of HIV I, and an antiligand to any one of said aforementioned antigens.

44. The process of claim 42 wherein the mammalian serum protein is bovine serum albumin.

45. The process of claims 37 or 44 wherein the dye is selected from the group consisting of Malachite Green, fluorescein, eosin, phenolphthalein, and erythrosin.

46. The process of claim 44 wherein the dye absorbs light in the visible spectrum.

47. The process of claim 46 wherein the dye is a triphenylmethyl type dye.

48. The process of claim 46 wherein the dye is Malachite Green.

49. A process for confirming that the actual concentration of a calibration or control material ("calibrator") is near its expected concentration in a solution that has been diluted from a stock solution comprising the steps of:
   a. combining an identifiably effective and non-interfering amount of marker ("the marker") and a predetermined quantity of a calibrator to form a marked stock calibrator solution having a first concentration of the marker and a second concentration of the calibrator, said marker being a dye conjugated to a carrier protein;
   b. calculating a proportion between the concentration of the marker and the concentration of the calibrator in the marked stock calibrator solution;
   c. diluting the marked stock calibrator solution or a portion thereof by a predetermined amount to produce a diluted calibrator solution wherein the proportion is substantially maintained, the diluted calibrator having a first expected concentration of the marker that is associated with a first expected physical parameter and further having a second expected concentration of the calibrator therein;
   d. measuring an actual physical parameter of the diluted calibrator solution, the actual physical parameter being proportional to the actual concentration of the marker therein;
   e. confirming that the actual concentration of calibrator in the diluted calibrator solution, as calculated from said actual physical parameter, is substantially near its expected concentration.

50. The process of claim 49 wherein the stock solution is an aqueous based solution.

51. The process of claim 42 wherein the calibrator is a ligand or an antiligand.

52. The process of claim 51 wherein the calibrator is selected from the group consisting of prostate specific antigen, human bone alkaline phosphatase antigen, human chorionic gonadotropin, follicle stimulating hormone, human leutenizing hormone, creatine phosphokinase MB isoenzyme, ferritin, carcinoembryonic antigen, hepatitis B surface antigen, hepatitis B surface antibody, hepatitis B core antigen, hepatitis B core antibody, hepatitis A virus antibody, hepatitis C virus antibody, the p41 antigen of HIV II, the gp120 antigen of HIV I, the p66 antigen of HIV I, the p41 antigen of HIV I, the p31 antigen of HIV I, the p24 antigen of HIV I, the p17 antigen of HIV I, and an antiligand to any one of said aforementioned antigens.

53. The process of claim 52 wherein the ratio of dye to carrier protein is within the range of from about 1:1 to about 15:1.

54. The process of claim 53 wherein the carrier protein is a mammalian serum protein.

55. The process of claims 49 or 54 wherein the mammalian serum protein is selected from the group consisting of bovine serum albumin, human serum albumin, porcine serum albumin, sheep serum albumin, murine serum albumin, goat serum albumin and guinea pig serum albumin.

56. The process of claim 55 wherein the mammalian serum protein is bovine serum albumin.

57. The process of claim 56 wherein the dye absorbs light in the visible spectrum.

58. The process of claim 57 wherein the dye is selected from the group consisting of Malachite Green, fluorescein, eosin, tetramethylrhodamine, and erythrosin.

59. The process of claim 58 wherein the dye is Malachite Green.

60. The process of claim 59 wherein the ratio of Malachite Green to bovine serum albumin is within the range from about 2.8:1 to about 7:1.

* * * * *

UNITED STATES PATENT AND TRADEMARK OFFICE
CERTIFICATE OF CORRECTION

PATENT NO. : 5447838
DATED : September 5, 1995
INVENTOR(S) : Meiklejohn, et al

It is certified that error appears in the above-indentified patent and that said Letters Patent is hereby corrected as shown below:

Column 3, line 37, "marked Stock" should be --marked stock--.

Column 8, line 14, "Chemistry, "Tietz" should be --Chemistry," Tietz--.

Column 8, line 32, "Chemistry, "Tietz N," should be --Chemistry," Tietz N.,--.

Column 15, line 45, "a piper," should be --a pipet,--.

Column 15, line 47, "the piper" should be --the pipet--.

Column 19, line 57, "1,5000," should be --1:5000,--.

Column 19, line 64, "control The" should be --control. The--.

Column 20, line 37, "then be added" should be --then added--.

UNITED STATES PATENT AND TRADEMARK OFFICE
CERTIFICATE OF CORRECTION

PATENT NO. : 5447838
DATED : September 5, 1995
INVENTOR(S) : Meiklejohn, et al

Page 2 of 2

It is certified that error appears in the above-indentified patent and that said Letters Patent is hereby corrected as shown below:

Column 22, line 39, "Preparation" should be --K. Preparation--.

Column 22, line 56, "Preparation" should be --L. Preparation--.

Column 26, lines 18-19, "claims 23 or 25" should be --claims 27 or 30--.

Column 28, line 40, "claim 42" should be --claim 49--.

Signed and Sealed this

Twelfth Day of November, 1996

Attest:

BRUCE LEHMAN

*Attesting Officer*        *Commissioner of Patents and Trademarks*